(12) United States Patent
Patt

(10) Patent No.: US 7,179,789 B2
(45) Date of Patent: *Feb. 20, 2007

(54) COMPOSITIONS AND METHODS FOR TREATMENT OF ROSACEA

(75) Inventor: Leonard M Patt, Seattle, WA (US)

(73) Assignee: ProCyte Corporation, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/123,823

(22) Filed: May 6, 2005

(65) Prior Publication Data

US 2005/0209130 A1 Sep. 22, 2005

Related U.S. Application Data

(62) Division of application No. 10/457,045, filed on Jun. 6, 2003, now Pat. No. 6,927,206.

(51) Int. Cl.
 *A61K 38/06* (2006.01)

(52) U.S. Cl. .............................. 514/6; 514/2

(58) Field of Classification Search ................ None
See application file for complete search history.

(56) References Cited

U.S. PATENT DOCUMENTS

| | | | |
|---|---|---|---|
| 4,665,054 A | 5/1987 | Pickart | 514/18 |
| 4,760,051 A | 7/1988 | Pickart | 514/6 |
| 4,767,753 A | 8/1988 | Pickart | 514/18 |
| 4,810,693 A | 3/1989 | Pickart | 514/18 |
| 4,877,770 A | 10/1989 | Pickart | 514/18 |
| 5,023,237 A | 6/1991 | Pickart | 514/18 |
| 5,059,588 A | 10/1991 | Pickart | 514/12 |
| 5,118,665 A | 6/1992 | Pickart | 514/6 |
| 5,120,831 A | 6/1992 | Pickart | 530/331 |
| 5,135,913 A | 8/1992 | Pickart | 514/16 |
| 5,164,367 A | 11/1992 | Pickart | 514/6 |
| 5,177,061 A | 1/1993 | Pickart | 514/18 |
| 5,214,032 A | 5/1993 | Pickart | 514/16 |
| 5,348,943 A | 9/1994 | Pickart | 514/18 |
| 5,538,945 A | 7/1996 | Pallenberg et al. | 514/6 |
| 5,550,183 A | 8/1996 | Pickart | 514/6 |
| 6,017,888 A | 1/2000 | Pallenberg et al. | 514/19 |
| 6,506,731 B1 | 1/2003 | Sandberg et al. | 514/15 |
| 6,927,205 B2 * | 8/2005 | Patt | 514/6 |
| 6,927,206 B2 * | 8/2005 | Patt | 514/6 |
| 2003/0087830 A1 | 5/2003 | Dupont et al. | 514/19 |

FOREIGN PATENT DOCUMENTS

| | | |
|---|---|---|
| EP | 0 577 151 A1 | 1/1994 |
| WO | WO 94/03482 | 2/1994 |
| WO | WO 03/030926 A1 | 4/2003 |

OTHER PUBLICATIONS

Maquart, F-X. et al, "In Vivo Stimulation of Connective Tissue Accumulation by the Tripeptide-Copper Complex Glycyl-L-Histidyl-L-Lysine-$Cu^{2+}$ in Rat Experimental Wounds," *J. Clin. Invest.* 92: 2368-2376, Nov. 1993.

Maquart, F-X. et al. "Stimulation of collagen Synthesis in Fibroblast Cultures by the Tripeptide-Copper Complex Glycyl-L-Histidyl-L-Lysine-$Cu^{2+}$," *FEBS Letters* 238(2):343-346, Oct. 1988.

Wegrowski, Y. et al., "Stimulation of Sulfated Glycosaminoglycan Synthesis by the Tripeptide-Copper Complex Glycyl-L-Histidyl-L-Lysine-$Cu^{2+}$," *Life Sciences* 51:1049-1056, 1992.

* cited by examiner

*Primary Examiner*—B. Dell Chism
(74) *Attorney, Agent, or Firm*—Seed IP Law Group PLLC

(57) ABSTRACT

A method for treating rosacea of the skin of a patient employs topically applying to the affected skin a composition comprising at least one peptide copper complex. In other embodiments, the present invention is directed to such a method where the composition used therefor further comprises certain disclosed active agents, including active drug and active cosmetic substances. In a related aspect, further embodiments of the present invention are directed to compositions comprising at least one peptide copper complex and certain active drug and active cosmetic substances that render the compositions particularly effective in treating rosacea.

1 Claim, No Drawings

COMPOSITIONS AND METHODS FOR TREATMENT OF ROSACEA

CROSS-REFERENCE TO RELATED APPLICATION

This application is a divisional of U.S. patent application Ser. No. 10/457,045, filed Jun. 6, 2003, now U.S. Pat. No. 6,927,206 now allowed, which application is incorporated herein by reference in its entirety.

BACKGROUND OF THE INVENTION

1. Field of the Invention

The present invention generally relates to the treatment of a dermatological condition and, more specifically, to the treatment of rosacea, by topical application of a composition comprising a peptide copper complex.

2. Description of the Related Art

Rosacea is a chronic inflammatory skin disorder characterized by four distinct clinical stages predominantly affecting the central aspect of the face. The first clinical evidence of rosacea is frequent and intense vasodilation or flushing. Most patients progress to a vascular stage characterized by an erythema that can persist for hours or days after a triggering event. Many patients remain stabilized at this stage while some progress to an inflammatory stage characterized by a symmetrical array of papules and pustules in addition to the persistent erythema. This stage can often become a chronic condition. A few patients, mostly male, can progress to the finals stage characterized by a distinctive hyperplasia or swelling, especially of the nose. Rosacea is a very visible skin condition that has a high impact on the quality of life of the patient. Treatments for rosacea commonly involve topical or oral antibiotics such as metronidazole and compounds such as sulfacetamide, sulfur, and azelaic acid. However, these and the other treatments for rosacea that are currently available, are all accompanied by various side effects, are costly, and/or involve long complicated treatment protocols. Accordingly, there remains a need in the art for more effective and otherwise improved methods for treating dermatological conditions related to rosacea by, for example, topically applying compositions, having a desired degree of effectivity, to areas of the skin of a patient in need hereof. The present invention fulfills this need and provides further related advantages.

BRIEF SUMMARY OF THE INVENTION

In brief, the present invention is directed to treating dermatological conditions related to rosacea by topically applying a composition comprising at least one peptide copper complex to an area of affected skin. It has been surprisingly found that such compositions, when topically applied, can substantially diminish the signs and symptoms of rosacea.

In one representative embodiment, the present invention is directed to a method for treating rosacea of skin, by topically applying to an area of skin in need thereof an effective amount of a composition comprising at least one peptide copper complex. Unexpectedly, topical application of an effective amount of such a composition to areas of skin in need of such treatment, results in significant reduction of the rosacea initially present on the area contacted.

In another representative embodiment, the present invention is directed to a method for such treatment where the at least one peptide copper complex is encapsulated in a liposome, microsponge, polymer matrix or other encapsulation technology adapted to aid in the delivery of the peptide copper complex to the areas of skin in need thereof, or to enhance the stability of the composition. In yet another representative embodiment, a method for such treatment is disclosed where the at least one peptide copper complex is formulated in an instrument adapted to deliver the peptide copper complex via iontophoresis or ultrasound to the areas of affected skin.

The present invention, in additional related embodiments, is directed to methods for treating rosacea of the skin of a patient where the topically applied composition used therefor further comprises, in one of the embodiments, an inert and physiologically-acceptable carrier or diluent in addition to the at least one peptide copper complex; and further comprises, in another of the embodiments, a skin lightening agent, a sunscreen agent, a skin conditioning agent, a skin protectant, an emollient, a humectant, or a mixture thereof in addition to the at least one peptide copper complex. In yet further related embodiments, the present invention is directed to such methods where the compositions used therefor further comprise, in addition to the at least one peptide copper complex, an active drug substance or an active cosmetic substance.

In additional embodiments, disclosed methods of the present invention utilize a composition comprising at least one peptide copper complex, where the composition, in one of the embodiments, further comprises an emulsifying agent, a surfactant, a thickening agent, an excipient, or a mixture thereof; and where the composition, in another of the embodiments, is in the form of a liquid, cream, gel, fluid cream, lotion, emulsion or microemulsion.

In a related aspect, the present invention is directed to a composition comprising at least one peptide copper complex and an active drug substance selected from the group consisting of a corticosteroid, metronidazole, sulfacetamide, sulfur, and azelaic acid; and to a composition comprising at least one peptide copper complex and an active cosmetic substance selected from the group consisting of allantoin, tocopherol, a tocopherol derivative, niacinamide, a phytosterol, an isoflavone, panthenol, a panthenol derivative, bisabolol, and farnesol.

These and other aspects of this invention will be evident upon reference to the following detailed description of the invention.

DETAILED DESCRIPTION OF THE INVENTION

As noted above, in one embodiment, disclosed is a method for treating rosacea of the skin of a patient by topically applying to an area of the skin in need thereof, an effective amount of a composition comprising at least one peptide copper complex. As used herein the word "treat," "treating" or "treatment"refers to using the compositions of the present invention either prophylactically to prevent outbreaks of rosacea symptoms, or therapeutically to ameliorate an existing condition characterized by rosacea. Also, as used herein, the word "patient" refers to a warm-blooded animal, including a human.

In more specific embodiments of the disclosed method of the present invention, the composition used therefor comprises at least one peptide copper complex that is L-alanyl-L-histidyl-L-lysine:copper(II) ("AHK-Cu"), L-valyl-L-histidyl-L-lysine:copper(II) ("VHK-Cu"), or glycyl-L-histidyl-L-lysine:copper(II) ("GHK-Cu"). As used herein, the expression "peptide copper complex" generally refers to a coordination compound comprising a peptide molecule and a copper(II) ion non-covalently complexed therewith. As is well understood in the art, copper (II) designates a copper ion having a valence of 2 (i.e., $Cu^{+2}$). The peptide molecule serves as the complexing agent by donating electrons to the copper ion to yield the non-covalent complex. The peptide molecule is a chain of two or more amino acid units or amino acid derivative units covalently bonded together via amide linkages (for example, —CONH—), the formation of such linkages being accompanied by the elimination of water.

Generally, an amino acid consists of an amino group, a carboxyl group, a hydrogen atom, and an amino acid side-chain moiety—all bonded, in the case of an alpha-amino acid, to a single carbon atom that is referred to as an alpha-carbon. The amino acid units may be provided by amino acids other than alpha-amino acids. For example, the amino acids may be beta- or gamma-amino acids, such as those shown below.

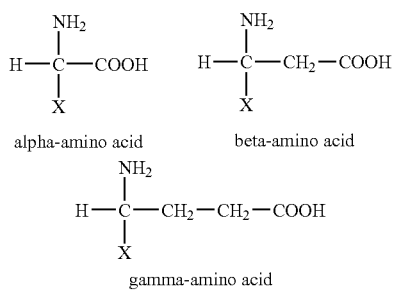

alpha-amino acid     beta-amino acid

gamma-amino acid where X is the amino acid side-chain moiety bonded, along with the amino group and hydrogen, to an alpha-, beta-, or gamma-carbon atom.

As another example, the amino acids include, but are not limited to, naturally occurring alpha-amino acids. Naturally occurring amino acids are those from which the amino acid units of naturally occurring proteins are derived. Some of these amino acids, along with their respective amino acid side chain moieties, are shown below in Table 1. The naturally occurring amino acids shown are all in the L configuration, referring to the optical orientation of the alpha carbon or other carbon atom bearing the amino acid side chain. A peptide molecule of the present invention may also comprise amino acids that are in the D optical configuration, or a mixture of D and L amino acids.

TABLE 1

Naturally Occurring Amino Acid Side-Chain Moieties

| Amino Acid Side Chain Moiety | Amino acid |
| --- | --- |
| —H | Glycine |
| —$CH_3$ | Alanine |
| —$CH(CH_3)_2$ | Valine |
| —$CH_2CH(CH_3)_2$ | Leucine |
| —$CH(CH_3)CH_2CH_3$ | Isoleucine |
| —$(CH_2)_4NH_3^+$ | Lysine |
| —$(CH_2)_3NHC(NH_2)NH_2^+$ | Arginine |
|  | Histidine |
| —$CH_2COO-$ | Aspartic Acid |
| —$CH_2CH_2COO-$ | Glutamic Acid |

TABLE 1-continued

Naturally Occurring Amino Acid Side-Chain Moieties

| Amino Acid Side Chain Moiety | Amino acid |
| --- | --- |
| —$CH_2CONH_2$ | Asparagine |
| —$CH_2CH_2CONH_2$ | Glutamine |
|  | Phenylalanine |
|  | Tyrosine |
| 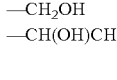 | Tryptophan |
| —$CH_2SH$ | Cysteine |
| —$CH_2CH_2SCH_3$ | Methionine |
| —$CH_2OH$ | Serine |
| —$CH(OH)CH_3$ | Threonine |
| 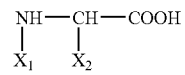 | Proline |

Other naturally occurring amino acids include hydroxyproline and gamma-carboxyglutamate.

Representative amino acid derivatives include those set forth in Table 2 below.

TABLE 2

Amino Acid Derivatives $$NH-CH-COOH$$
$$\;\;|\;\;\;\;\;\;|$$
$$\;X_1\;\;\;X_2$$

Where $X_2$ = H or the following moieties:
—$(CH_2)_nCH_3$ where n = 1–20
—$(CH_2)_nCH(CH_3)(CH_2)_mCH_3$ where n, m = 0–20 (when n = 0, m ≠ 0 or 1 and when n = 1, m ≠ 0)
—$(CH_2)_nNH_2$ where = 1–20 (n ≠ 4)
—$(CH_2)_nCONH_2$ where n = 3–20
—$(CH_2)_nCOOH$ where n = 3–20

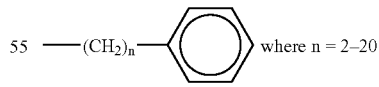 where n = 2–20

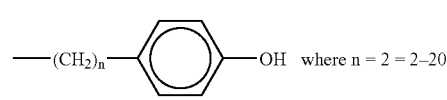 where n = 2 = 2–20

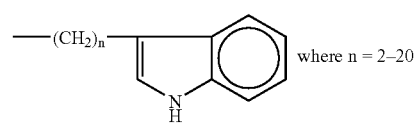 where n = 2–20

TABLE 2-continued

Amino Acid Derivatives

NH—CH—COOH
 |      |
 X₁    X₂

—$(CH_2)_nSH$ where n = 2–20
—$(CH_2)_nS(CH_2)_mCH_3$ where n, m = 1–20 (when n = 2, m ≠ 0)
—$(CH_2)_nCH_2OH$ where n = 1–20
—$(CH_2)_nCH(CH_3)OH$ where n = 1–20
And where $X_1$ = H or the following moieties:
—$(CH_2)_nCH_3$ where n = 0–20
—$(CH_2)_nCH(CH_3)(CH_2)_mCH_3$ where n, m = 0–20

Histidine derivatives include compounds having the structure:

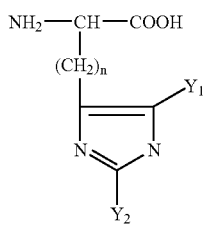

where n=1–20, and $Y_1$ and $Y_2$ are independently selected from alkyl moieties containing from 1–12 carbon atoms or an aryl moiety containing from 6–12 carbon atoms. In certain embodiments, n is 1, $Y_2$ is methyl, and $Y_1$ is H (i.e., 3-methyl histidyl) or $Y_2$ is H and $Y_1$ is methyl (i.e., 5-methyl histidine).

As used herein, "alkyl" means a straight chain or branched, cyclic or noncyclic, substituted or unsubstituted, saturated or unsaturated aliphatic hydrocarbon containing from 1 to 18 carbon atoms. Representative saturated straight chain alkyls include methyl, ethyl, n-propyl and the like, while saturated branched alkyls include isopropyl, sec-butyl, isobutyl, tert-butyl, isopentyl, and the like. Representative saturated cyclic alkyls include cyclopropyl, cyclobutyl, cyclopentyl, —$CH_2$cyclohexyl, and the like; while unsaturated cyclic alkyls include cyclopentenyl, cyclohexenyl, and the like. Unsaturated alkyls contain at least one double or triple bond between adjacent carbon atoms (referred to as an "alkenyl" or "alkynyl," respectively). Representative alkenyls include ethylenyl, 1-butenyl, isobutylenyl, 2-methyl-2-butenyl, and the like; while representative alkynyls include acetylenyl, 2-butynyl, 3-methyl-1-butynyl, and the like.

Also, as used herein, "aryl" means an aromatic carbocyclic moiety such as phenyl or naphthyl, and may be substituted or unsubstituted. "Arylalkyl," as used herein, means an alkyl having at least one alkyl hydrogen atom replaced with a substituted or unsubstituted aryl moiety, such as benzyl (i.e., —$CH_2$phenyl,—$(CH_2)_2$phenyl, —$(CH_2)_3$phenyl, —$CH(phenyl)_2$, and the like).

Similarly, arginine derivatives include compounds having the structure:

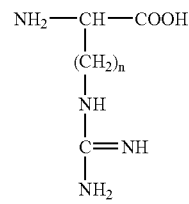

where n=1–20 (excluding n=3).

A peptide copper complex of the present invention may have the formula $[R_1—R_2—R_3]$:copper(II) where $R_3$ is at least one amino acid or amino acid derivative, as defined above, bonded to $R_2$ by a peptide bond (i.e., —C(═O) NH—). Where $R_3$ is a single amino acid or amino acid derivative, then the peptide of the peptide copper complex is generally classified as a tripeptide. As another example of a peptide copper complex of the present invention having the formula $[R_1—R_2—R_3]$:copper(II), $R_3$ is a chemical moiety bonded to the $R_2$ moiety by an amide bond. The expression "chemical moiety," as used herein and with reference to $R_3$, includes any chemical moiety having an amino group capable of forming an amide bond with the carboxyl terminus of $R_2$ (i.e., the carboxyl terminus of histidine, arginine, or derivatives thereof).

As a more particular example, where $R_3$ is a chemical moiety bonded to the $R_2$ moiety by an amide bond, $R_3$ is —$NH_2$, an alkylamino moiety having from 1–20 carbon atoms, or an arylamino moiety having from 6–20 carbon atoms. As used herein, an "alkylamino moiety" encompasses alkyl moieties containing an amino moiety, wherein the alkyl moiety is as defined above, and includes, but is not limited to, octyl amine and propyl amine. Similarly, an "arylamino moiety" encompasses aryl moieties containing an amino moiety, wherein the aryl moiety is as defined above, and includes, but is not limited to, benzylamine and benzyl-$(CH_2)_{1-14}$-amine. Further examples of suitable chemical moieties having amino groups capable of forming an amide linkage with the carboxyl terminus of $R_2$ include polyamines such as spermine and sperimidine.

It should be understood that $R_3$ may include more than one chemical moiety. For example, additional amino acids or amino acid derivatives may be bonded to the above-described peptide copper complexes comprising tripeptides to yield peptide copper complexes comprising peptides having four or more amino acids and/or amino acid derivatives. For purposes of illustration, Table 3, shown below, presents various representative examples of peptide copper complexes used for or comprised in embodiments of the present invention.

TABLE 3

Representative Peptide-Copper Complexes

Examples of [R₁—R₂]:copper(II)

| | |
|---|---|
| glycyl-histidine:copper | alanyl-histidine:copper |
| glycyl-(3-methyl)histidine:copper | alanyl-(3-methyl)histidine:copper |
| glycyl-(5-methyl)histidine:copper | alanyl-(5-methyl)histidine:copper |
| glycyl-arginine:copper | alanyl-arginine:copper |
| (N-methyl)glycine-histidine:copper | (N-methyl)glycine-arginine:copper |

Examples of [R₁—R₂—R₃]:copper(II) where R₃ is a Chemical Moiety Linked by Amide Bond

| | |
|---|---|
| glycyl-histidyl-NH₂:copper | glycyl-arginyl-NH₂:copper |
| glycyl-(3-methyl)histidyl-NH₂:copper | alanyl-(3-methyl)histidyl-NH₂:copper |
| glycyl-arginyl-NH₂:copper | alanyl-arginyl-NH₂:copper |
| (N-methyl)glycine-histidyl-NH₂:copper | (N-methyl)glycine-arginyl-NH₂:copper |
| glycyl-histidyl-NHoctyl:copper | glycyl-arginyl-NHoctyl:copper |

Examples of [R₁—R₂—R₃]:copper(II) where R₃ is an Amino Acid or Amino Acid Derivative Linked by Peptide Bond

| | |
|---|---|
| glycyl-histidyl-lysine:copper | glycyl-arginyl-lysine:copper |
| glycyl-(3-methyl)histidyl-lysine:copper | glycyl-(5-methyl)histidyl-lysine:copper |
| alanyl-histidyl-lysine:copper | alanyl-arginyl-lysine:copper |
| alanyl-(3-methyl)histidyl-lysine:copper | alanyl-(5-methyl)histidyl-lysine:copper |
| glycyl-histidyl-phenylalanine:copper | glycyl-arginyl-phenylalanine:copper |
| glycyl-(3-methyl)histidyl-phenylalanine:copper | glycyl-(5-methyl)histidyl-phenylalanine:copper |
| alanyl-histidyl-phenylalanine:copper | alanyl-arginyl-phenylalanine:copper |
| alanyl-(3-methyl)histidyl-phenylalanine:copper | alanyl-(5-methyl)histidyl-phenylalanine:copper |
| glycyl-histidyl-lysyl-phenylalanyl-phenylalanyl:copper | glycyl-arginyl-lysyl-phenylalanyl-phenylalanyl:copper |
| glycyl-(3-methyl)histidyl-lysyl-phenylalanyl-phenylalanyl:copper | glycyl-(5-methyl)histidyl-lysyl-phenylalanyl-phenylalanyl:copper |
| (N-methyl)glycyl-histidyl-lysine:copper | (N-methyl)glycyl-arginyl-lysine:copper |
| valyl-histidyl-lysine:copper | glycyl-histidyl-lysyl-prolyl-phenylalanyl-proline:copper |
| prolyl-histidyl-lysine:copper | Leucyl-histidyl-lysine:copper |
| glycyl-D-histidyl-L-lysine:copper | |
| seryl-histidyl-lysine:copper | |

Further examples of peptide copper complexes encompassed in embodiments of the present invention are disclosed in U.S. Pat. Nos. 4,665,054; 4,760,051; 4,767,753; 4,810,693; 4,877,770; 5,023,237; 5,059,588; 5,118,665; 5,120,831; 5,164,367; 5,177,061; 5,214,032; 5,538,945; 5,550,183; and 6,017,888, all of which are incorporated herein by reference in their entirety.

Examples of the peptide copper complex derivatives, encompassed in embodiments of the present invention, include, but are not limited to, those disclosed and described in the above-cited U.S. Patents that are directed to peptide copper complexes, as well as those disclosed and described in the published PCT application having the international publication number WO 94/03482, incorporated herein by reference in its entirety.

Copper is known to have many beneficial biological applications, including wound healing, treating inflammatory conditions, and effecting cosmetic improvements by, for example, stimulating a variety of processes related to skin, such as collagen, elastin and glycosaminoglycan production (see, e.g., Maquart, F. X., Pickart, L., Laurent, M., Gillery, P., Monboisse, J. C., Borel, J. P., "Stimulation of Collagen Synthesis in Fibroblast Cultures by the Tripeptide-Copper Complex Glycyl-L-Histidyl-L-Lysine-Copper(2+)," FEBS Lett. 238(2): 343–346, 1988; Wegrowski, Y., Maquart, F. X. and Borel, J. P., "Stimulation of Sulfated Glycosaminoglycan Synthesis by the Tripeptide-Copper Complex Glycyl-L-Histidyl-L-Lysine-Copper(2+), " Life Sciences 51: 1049–1056, 1992; Maguart, F. X., Bellon, G., Chaqour, B., Wegrowski, J., Patt L. M., Trachy, R. E., Monboisse, J. C., Chastang, F., Birembaut, P., Gillery, P. and Borel, J. P., "In Vivo Stimulation of Connective Tissue Accumulation by the Tripeptide-Copper Complex Glycyl-L-Histidyl-L-Lysine-Copper(2+) in Rat Experimental Wounds," J. Clin. Invest. 92: 2368–2376, 1993). The above-cited references are incorporated herein by reference in their entireties.

Copper salts alone are ineffective, or even inhibitory, for such applications. The copper must be delivered in a biologically acceptable form. As an example, when copper is complexed with a biologically acceptable carrier molecule, such as a peptide, it may then be effectively delivered to cells to provide beneficial biological applications such as those mentioned above. As more specific examples, peptide copper complexes that are useful for wound healing and skin health are disclosed in U.S. Pat. Nos. 4,760,051; 4,665,054; 4,877,770; 5,135,913; and 5,348,943, as well as in U.S. patent application Ser. No. 60/327,371.

The synthesis of the above-disclosed peptide copper complexes is described in detail in the above-referenced patents. For example, the peptides of the peptide copper complexes disclosed herein may be synthesized by either solution or solid phase techniques known to one skilled in the art of peptide synthesis. The general procedure involves the stepwise addition of protected amino acids to build up the desired peptide sequence. The resulting peptide may then be complexed to copper (at the desired molar ratio of peptide to copper) by dissolving the peptide in water, followed by the addition of copper chloride or other suitable copper salt and adjusting the pH to greater than 4.0.

Aqueous solutions of peptide copper complexes are prepared by methods that are well known to one skilled in the art. For example, an amount of dried peptide copper complex, suitable for a desired concentration, is readily dissolved in water with mixing and gentle heating. An alternative method is to prepare a solution of the desired peptide, followed by the addition of a copper salt in the desired molar ratio to yield the desired solution of the peptide copper complex. Examples of copper salts that may be used are cupric chloride and cupric acetate. When aqueous solutions of peptide copper complexes are prepared, the solutions are neutralized, typically with NaOH.

In yet another embodiment of the method of the present invention, the peptide portion of the at least one peptide copper complex used therefor may also be of natural origin. In this embodiment, the peptide is formed by the hydrolysis of naturally occurring proteins, polypeptides, or larger peptides of either plant, microbial, or animal origin. Hydrolysis may be by enzymatic treatment or by acid or base hydrolysis. The copper complex of this type of peptide copper complex is formed by addition of a suitable copper salt to the aqueous solution of the peptide. Alternatively, the peptide copper complex may be formed during the manufacturing of a formulation by separate additions of the peptide and copper salt in a suitable solvent.

In more particular embodiments of the disclosed methods of the present invention, the composition used therefor comprises at least one peptide copper complex where the concentration of the latter, by weight of the composition, ranges from about 0.01% to about 5%; from about 0.025% to about 1%; or from about 0.05% to about 0.5%. In further, more particular embodiments, the molar ratio of peptide to copper in the peptide copper complex ranges from about 1:1 to about 3:1 in one such embodiment, and from about 1:1 to about 2:1 in another such embodiment.

In additional embodiments of the method disclosed herein, the composition used therefor comprises at least one peptide copper complex that, in one embodiment, is encapsulated in a liposome or microsponge adapted to aid in the delivery of the peptide copper complex to the area of the skin being treated; and, in another embodiment, is formulated in an instrument adapted to deliver the peptide copper complex to the area of the skin via iontophoresis.

In view of the previously noted beneficial health and cosmetic applications of compositions comprising peptide copper complexes, the compositions used for the methods of the present invention, in certain embodiments, are formulated for use as pharmaceutical or cosmetic products. Accordingly, the method of the present invention, in another embodiment, uses a composition as disclosed above, but further comprising an inert and physiologically-acceptable carrier or diluent, where, in a related, more specific embodiment, the carrier or diluent is water, physiological saline, bacteriostatic saline, a pharmaceutically or cosmetically acceptable gel or cream, a short chain alcoholic solution, or a short chain glycol.

Further, the compositions used for the inventive method disclosed herein comprise, in addition to at least one peptide copper complex an active agent. The expression "active agent," as used herein, refers to a compound or substance that provides benefits to the skin and/or provides desirable properties to a composition formulated as a cosmetic preparation. Active agents include, as examples, active drug substances, active cosmetic substances, sunscreen agents, skin lightening agents, tanning agents skin conditioning agents, skin protectants, emollients and humectants. In one embodiment, the active agent is an active drug substance that, in a particular related embodiment, is a corticosteroid, coal tar, anthralin, calcipotriene, and tarzarotene. The expression, "active drug substance," as used herein, refers to a chemical or biological moiety that has been shown to alter either the composition or function of the body.

In yet another embodiment, the active agent is an active cosmetic substance. The expression, "active cosmetic substance," as used herein, refers to compounds, mixtures, or extracts that have various positive effects on the skin of a patient. In related, more particular embodiments, the active cosmetic substance is, in one such embodiment, retinol, retinoic acid, or a derivative thereof; and, in another such embodiment, the active cosmetic substance is allantoin, tocopherol, tocopherol derivatives, niacinamide, phytosterols, isoflavones, panthenol, panthenol derivatives, bisabolol and farnesol.

In a further related and more particular embodiment, the active cosmetic substance is a phytochemical compound. As is well understood by one of ordinary skill in the art, a phytochemical compound may either be in a purified form or as present in extracts derived from various plants. Examples of phytochemical cosmetically-active substances include, but are not limited to, any of the anti-oxidant pigments that are naturally present in, and impart color to, fruits and vegetables, as well present in the roots, bark, leaves, flowers and seeds of plants. Polyphenols and carotenoids are examples of phytochemical compounds. Flavanoids, flavonoids and their derivatives, flavolignans and polyphenolic rhizomes, represent some of the more significant polyphenols, with regard to having potent anti-oxidant and anti-inflammatory properties. Examples of plant extracts that provide such active cosmetic substances are extracts of the genus *Camellia*, including *Camellia sinensis* (i.e., green tea) and *Camellia assaimic*, licorice, sea whip, aloe vera, chamomile, and the like.

In a further specific embodiment of the disclosed method that uses a composition comprising at least one peptide copper complex and an active agent, the latter is a skin lightening agent, a sunscreen agent, a skin conditioning agent, a skin protectant, an emollient, a humectant, or a mixture thereof. Suitable sunscreen agents absorb, reflect, or scatter radiation in the UV range at wavelengths ranging from 290 to 400 nanometers. Specific examples include, but are not limited to, benzophenone-3 (oxybenzone), benzophenone4 (sulisobenzone), benzophenone-8 (dioxybenzone), butyl methoxydibenzoylmethane (Avobenzone), DEA-methoxycinnamate (diethanolamine methoxycinnamate), ethyl dihydroxypropyl PABA (ethyl 4-[bis(hydroxypropyl)] aminobenzoate), ethylhexyl dimethyl PABA (Padimate O), ethylhexyl methoxycinnamate (octyl methoxycinnamate), ethylhexyl salicylate (octyl salicylate), homosalate, menthyl anthranilate (Meradimate), octocrylene, PABA (aminobenzoic acid), phenylbenzimidazole sulfonic acid (Ensulizole), TEA-salicylate (trolamine salicylate), titanium dioxide, and zinc oxide. One skilled in the art will appreciate that other sunscreen agents may be included in the compositions used for the methods of the present invention.

Suitable skin lightening agents include, but are not limited to, ascorbic acid and derivatives thereof; kojic acid and derivatives thereof; hydroquinone; azelaic acid; and various plant extracts, such as those from licorice, grape seed, and bear berry. Those skilled in the art will appreciate that other skin lightening agents may be included in the compositions used for some of the methods of the present invention.

As noted for the above-disclosed specific embodiment of the method of the present invention, the composition used therefor may comprise a skin conditioning agent. Such an agent typically comprises a substance that enhances the appearance of dry or damaged skin, as well as a material that adheres to the skin to reduce flaking, restore suppleness, and generally improve the appearance of skin. Representative examples of a skin conditioning agent that may be used include: acetyl cysteine, N-acetyl dihydrosphingosine, acrylates/behenyl acrylate/dimethicone acrylate copolymer, adenosine, adenosine cyclic phosphate, adenosine phosphate, adenosine triphosphate, alanine, albumen, algae extract, allantoin and derivatives, aloe barbadensis extracts, amyloglucosidase, arbutin, arginine, bromelain, buttermilk powder, butylene glycol, calcium gluconate, carbocysteine, carnosine, beta-carotene, casein, catalase, cephalins, ceramides, chamomilla recutita (matricaria) flower extract, cholecalciferol, cholesteryl esters, coco-betaine, corn starch modified, crystallins, cycloethoxymethicone, cysteine DNA, cytochrome C, darutoside, dextran sulfate, dimethicone copolyols, dimethylsilanol hyaluronate, elastin, elastin amino acids, ergocalciferol, ergosterol, fibronectin, folic acid, gelatin, gliadin, beta-glucan, glucose, glycine, glycogen, glycolipids, glycoproteins, glycosaminoglycans, glycosphingolipids, horseradish peroxidase, hydrogenated proteins, hydrolyzed proteins, jojoba oil, keratin, keratin amino acids, and kinetin.

Other non-limiting examples of a skin conditioning agent that may be included in the compositions used for the present invention are: lactoferrin, lanosterol, lecithin, linoleic acid, linolenic acid, lipase, lysine, lysozyme, malt extract, maltodextrin, melanin, methionine, niacin, niacinamide, oat amino acids, oryzanol, palmitoyl hydrolyzed proteins, pancreatin, papain, polyethylene glycol, pepsin, phospholipids, phytosterols, placental enzymes, placental lipids, pyridoxal 5-phosphate, quercetin, resorcinol acetate, riboflavin, saccharomyces lysate extract, silk amino acids, sphingolipids, stearamidopropyl betaine, stearyl palmitate, tocopherol, tocopheryl acetate, tocopheryl linoleate, ubiquinone, vitis vinifera (grape) seed oil, wheat amino acids, xanthan gum, and zinc gluconate. A skin conditioning agent, other than those listed above, may also be used, as is readily appreciated by those skilled in the art.

Also, as noted above, the composition used for a disclosed method may include a skin protectant, defined herein as a compound that protects injured or exposed skin or mucous membrane surfaces from harmful or irritating external compounds. Representative examples thereof include: algae extract, allantoin, aluminum hydroxide, aluminum sulfate, camellia sinensis leaf extract, cerebrosides, dimethicone, glucuronolactone, glycerin, kaolin, lanolin, malt extract, mineral oil, petrolatum, potassium gluconate, and talc. Those skilled in the art will readily appreciate that a skin protectant, other than those listed above, may be included in the compositions used.

An emollient, as the term is used herein, is a cosmetic ingredient that can help skin maintain a soft, smooth, and pliable appearance. Emollients are able to provide these benefits, largely owing to their ability to remain on the skin surface, or in the stratum corneum, to act as a lubricant and reduce flaking. Some examples of an emollient, suitable for use in the above-disclosed, specific embodiment of this invention, are: acetyl arginine, acetylated lanolin, algae extract, apricot kernel oil polyethylene glycol-6 esters, avocado oil polyethylene glycol-11 esters, bis-polyethylene glycol-4 dimethicone, butoxyethyl stearate, $C_{18}$-$C_{36}$ acid glycol ester, $C_{12}$-$C_{13}$ alkyl lactate, caprylyl glycol, cetyl esters, cetyl laurate, coconut oil polyethylene glycol-10 esters, di-$C_{12}$-$C_{13}$ alkyl tartrate, diethyl sebacate, dihydrocholesteryl butyrate, dimethiconol, dimyristyl tartrate, disteareth-5 lauroyl glutamate, ethyl avocadate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, isostearyl neopentanoate, isostearyl palmitate, isotridecyl isononanoate, laureth-2 acetate, lauryl polyglyceryl-6 cetearyl glycol ether, methyl gluceth-20 benzoate, mineral oil, myreth-3 palmitate, octyldecanol, octyldodecanol, odontella aurita oil, 2-oleamido-1,3 octadecanediol, palm glycerides, polyethylene glycol avocado glycerides, polyethylene glycol castor oil, polyethylene glycol-22/dodecyl glycol copolymer, polyethylene glycol shea butter glycerides, phytol, raffinose, stearyl citrate, sunflower seed oil glycerides, and tocopheryl glucoside. Those skilled in the art will readily appreciate that emollients, other than those listed above, may also be used.

Humectants are cosmetic ingredients that help maintain moisture levels in skin. Some examples of suitable humectants are: acetyl arginine, algae extract, aloe barbadensis leaf extract, 2,3-butanediol, chitosan lauroyl glycinate, diglycereth-7 malate, diglycerin, diglycol guanidine succinate, erythritol, fructose, glucose, glycerin, honey, hydrolyzed wheat protein/polyethylene glycol-20 acetate copolymer, hydroxypropyltrimonium hyaluronate, inositol, lactitol, maltitol, maltose, mannitol, mannose, methoxy polyethylene glycol, myristamidobutyl guanidine acetate, polyglyceryl sorbitol, potassium pyrollidone carboxylic acid (PCA), propylene glycol, sodium pyrollidone carboxylic acid (PCA), sorbitol, sucrose, and urea. Other humectants may be used for yet additional embodiments of this invention, as will be appreciated by those skilled in the art.

In a further specific embodiment of the method of the present invention, the composition used therefor comprises a fatty alcohol, a fatty acid, an organic base, an inorganic base, a preserving agent, a wax ester, a steroid alcohol, a triglyceride ester, a phospholipid, a polyhydric alcohol ester, a fatty alcohol ether, a hydrophilic lanolin derivative, a hydrophilic beeswax derivative, a cocoa butter wax, a silicon oil, a pH balancer, a cellulose derivative, a hydrocarbon oil, or a mixture thereof. Non-limiting examples of a suitable phospholipid include lecithin and cephalin. Suitable hydrocarbon oils include, but are not limited to, palm oil, coconut oil, and mineral oil.

Additional ingredients may be included in the above compositions to vary the texture, viscosity, color and/or appearance thereof, as is appreciated by one of ordinary skill in the art. Accordingly, in a further embodiment, the present invention is directed to a disclosed method that utilizes a composition where the latter comprises, in addition to at least one peptide copper complex, an emulsifying agent, a surfactant, a thickening agents, and surfactants.

As a specific example, an emulsifier and a surfactant may be included in a composition used for the present invention that is formulated as an emulsion. Either a water-in-oil or oil-in-water emulsion may be formulated. Examples of suitable surfactants and emulsifying agents include: non-ionic ethoxylated and nonethoxylated surfactants, abietic acid, almond oil polyethylene glycol, beeswax, butylglucoside caprate, $C_{18}$-$C_{36}$ acid glycol ester, $C_9$-$C_{15}$ alkyl phosphate, caprylic/capric triglyceride polyethylene glycol4 esters, ceteareth-7, cetyl alcohol, cetyl phosphate, corn oil polyethylene glycol esters, dextrin laurate, dilaureth-7 citrate, dimyristyl phosphate, glycereth-17 cocoate, glyceryl erucate, glyceryl laurate, hydrogenated castor oil polyethylene glycol esters, isosteareth-11 carboxylic acid, lecithin, lysolecithin, nonoxynol-9, octyldodeceth-20, palm glyceride, polyethylene glycol diisostearate, polyethylene glycol stearamine, poloxamines, potassium linoleate, raffinose myristate, sodium caproyl lactylate, sodium caprylate, sodium cocoate, sodium isostearate, sodium tocopheryl phosphate, steareths, and trideceths. Other surfactants and emulsifiers may be used, as will be appreciated by one of ordinary skill in the art.

Examples of a thickening (ie., viscosity increasing) agent that is suitable for inclusion in the composition used for the above-disclosed embodiment, include, but are not limited to, those agents commonly used in skin care preparations. More specifically, such examples include acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxyethylcellulose, hydroxypropylcellulose, hydroxpropyl starch, magnesium alginate, methylcellulose, microcrystalline cellulose, pectin, various polyethylene glycol's, polyacrylic acid, polymethacrylic acid, polyvinyl alcohol, various polypropylene glycols, sodium acrylates copolymer, sodium carrageenan, xanthan gum, and yeast beta-glucan. Thickening agents other than those listed above may also be used in related embodiments of the present invention.

As heretofore noted, the compositions used for the methods of the present invention are applied topically to human skin. Accordingly, such a composition is formulated, in a further embodiment, as a liquid, cream, gel, oil, fluid cream or milk, lotion, emulsion, or microemulsion. In a related embodiment, the composition further comprises an excipient adapted for application to the face and neck. Such an excipient should have a high affinity for the skin, be well tolerated, stable, and yield a consistency that allows for easy and pleasant utilization.

Typically, for a method of the present invention, a small amount of the composition (from about 0.1 ml to about 5 ml) used therefor is applied to exposed areas of affected skin from a suitable container or applicator, and, if necessary, the composition is then spread over and/or rubbed into the skin using the hand, finger, or other suitable device. Each composition disclosed herein is typically packaged in a container that is appropriate in view of its viscosity and intended use by the patient. For example, a lotion or fluid cream may be packaged in a bottle, roll-ball applicator, capsule, propellant-driven aerosol device, or a container fitted with a manually operated pump. A cream may simply be stored in a non-deformable bottle, or in a squeeze container, such as a tube or a lidded jar.

In a related aspect, the present invention is also directed to pharmaceutical compositions having utility for treating rosacea when topically applied to affected areas of the skin of a patient. In one embodiment, the composition comprises at least one peptide copper complex and an active drug substance selected from the group consisting of corticosteroids, coal tar, anthralin, calcipotriene, and tazarotene. In another embodiment, the composition comprises at least one peptide copper complex and an active cosmetic substance selected from the group consisting of allantoin, tocopherol, tocopherol derivatives, niacinamide, phytosterols, isoflavones, panthenol, panthenol derivatives, bisabolol and farnesol.

The following examples are provided for the purpose of illustration, not limitation.

EXAMPLES

The examples that follow illustrate the preparation, characterization and utility of certain compositions used for exemplary embodiments of the methods of the present invention; and illustrate the effectiveness of such methods in treating rosacea of the skin of a human patient.

Example 1

The composition of a representative moisturizing lotion used for a method of the present invention is shown below.

| Ingredients | % w/w |
|---|---|
| Water | 73.80% |
| glycerin | 1.00% |
| xanthan gum | 0.50% |
| diisopropyl adipate | 4.00% |
| isocetyl stearate | 6.00% |
| octyl palmitate | 10.00% |
| glyceryl stearate | 1.00% |
| cetyl alcohol | 1.00% |
| stearyl alcohol | 0.80% |
| behenyl alcohol | 0.50% |
| palmitic acid | 0.25% |
| stearic acid | 0.25% |
| glycyl-L-histidyl-L-lysine:copper(II) | 0.30% |
| propylene glycol | 0.55% |
| diazolidinyl urea | 0.03% |
| iodopropynyl butylcarbonate | 0.02% |
| Total | 100.00% |

Example 2

The composition of a representative moisturizing cream used for a method of the present invention is shown below.

| Ingredients | % w/w |
|---|---|
| water | 77.35% |
| ethylhexyl palmitate | 8.00% |
| octyldodecanol | 2.50% |
| butyloctyl calicylate | 2.00% |
| squalane | 1.50% |
| jojoba oil | 0.50% |
| tocopheryl acetate | 0.20% |
| bisabolol | 0.20% |
| polyacrylamide | 1.50% |
| laureth-7 | 0.50% |
| glycerin | 3.00% |
| panthenol | 0.60% |
| allantion | 0.10% |
| cyclomethicone | 0.50% |
| carbomer | 0.10% |
| polysorbate 20 | 0.20% |
| L-alanyl-L-histidyl-L-lysine:copper(II) | 0.25% |
| propylene glycol | 0.56% |
| diazolidinyl urea | 0.30% |
| methylparaben | 0.11% |
| propylparaben | 0.03% |
| Total | 100.00% |

Example 3

The composition of a representative moisturizing body lotion used for a method of the present invention is shown below.

| Ingredients | % w/w |
|---|---|
| water | 74.40% |
| hydrogenated vegetable oil | 6.00% |
| canola oil | 4.00% |
| polyoxyethylene stearyl stearate | 4.00% |
| steareth-21 | 2.00% |
| octyldodecanol | 6.00% |
| sorbeth-30 | 2.50% |
| glycyl-L-histidyl-L-lysine:copper(II) | 0.10% |
| propylene glycol | 0.56% |
| diazolidinyl urea | 0.30% |
| methylparaben | 0.11% |
| propylparaben | 0.03% |
| Total | 100.00% |

Example 4

The composition of a representative water-in-oil emulsion used for a method of the present invention is shown below.

| Ingredients | % w/w |
|---|---|
| water | 71.84% |
| quarternium 82 | 2.00% |
| polyquarternium-37 | 1.10% |
| mineral oil | 0.50% |
| PPG-1-trideceth-6 | 0.40% |
| ethylhexyl isononanoate | 20.00% |
| cetyl dimethicone copolyol | 1.00% |
| L-alanyl-L-histidyl-L-lysine:copper(II) | 0.10% |
| kojic Acid | 2.0% |
| propylene glycol | 0.56% |
| imidazolidinyl urea | 0.30% |
| methylparaben | 0.11% |
| propylparaben | 0.03% |
| butylparaben | 0.02% |
| isopropylparaben | 0.02% |
| isobutylparaben | 0.02% |
| Total | 100.00% |

Example 5

The composition of a representative oil-in-water emulsion type face cream used for a method of the present invention is shown below.

| Ingredients | % w/w |
|---|---|
| water | 75.20% |
| glycerin | 4.00% |
| steareth-100 | 0.60% |
| steareth-2 | 0.35% |
| xanthan gum | 0.35% |
| isopropyl palmitate | 4.00% |
| Isohexanodecane | 1.00% |
| isostearyl isostearate | 1.20% |
| octyl dodecanol | 1.00% |
| stearic acid | 2.50% |
| cetostearyl alcohol | 2.50% |
| petrolatum | 4.00% |
| glycyl-L-histidyl-L-lysine:copper(II) | 0.10% |
| phenoxyethanol | 3.00% |
| methylparaben | 0.11% |
| propylparaben | 0.03% |
| butylparaben | 0.02% |

-continued

| Ingredients | % w/w |
|---|---|
| isopropylparaben | 0.02% |
| isobutylparaben | 0.02% |
| Total | 100.00% |

Example 6

The composition of a representative high silicon content cream used for a method of the present invention is shown below.

| Ingredients | % w/w |
|---|---|
| water | 44.25% |
| dimethicone | 50.00% |
| behentriomnium methosulfate | 4.00% |
| cetearyl alcohol | 2.00% |
| glycyl-L-histidyl-L-lysine:copper(II) | 0.20% |
| methylparaben | 0.30% |
| ethylparaben | 0.10% |
| propylparaben | 0.03% |
| butylparaben | 0.02% |
| Total | 100.00% |

Example 7

The composition of a representative moisturizing cream used for a method of the present invention is shown below.

| Ingredients | % w/w |
|---|---|
| Water | 78.13 |
| Glyceryl Stearate | 3.5 |
| Stearic Acid | 2.75 |
| Cetyl Alcohol | 2.5 |
| Sodium Behenoyl Lactylate | 2.47 |
| Octyldodecyl Neopentanoate | 2 |
| $C_{12-15}$ Alkyl Benzoate | 2 |
| Cyclomethicone | 1.5 |
| Dimethicone | 1.5 |
| Glycyl-Histidyl-Lysine Copper Complex | 0.25 |
| Sodium Carboxymethyl Betaglucan | 0.25 |
| Camellia Oleifera Extract | 0.1 |
| Tocopheryl Acetate | 0.25 |
| Sodium Hyaluronate | 0.15 |
| Vitis Vinifera (Grape) Seed Oil | 0.25 |
| Squalane | 0.25 |
| Prunus Armeniaca (Apricot) Kernel Oil | 0.25 |
| Ethylhexyl Stearate | 0.2 |
| Propylene Glycol Isoceteth-3 Acetate | 0.5 |
| Propylene Glycol | 0.56 |
| Hydroxyethylcellulose | 0.15 |
| Isopropylparaben | 0.02 |
| Isobutylparaben | 0.02 |
| Butylparaben | 0.02 |
| Diazolidinyl Urea | 0.3 |
| Methylparaben | 0.1 |
| Propylparaben | 0.03 |
| Total | 100.00% |

Example 8

The utility of the composition of Example 7 was demonstrated in a 12 week study involving 8 human patients. More specifically, the cream of Example 7, containing glycyl-L-histidyl-L-lysine:copper(II), was tested for its effect on rosacea. The cream was applied as a thin film to the face twice each day, once in the morning and once at night.

At the beginning of the study, and at weeks 6 and 12, the number of inflammatory lesions (papules and pustules) was determined at the beginning of the study, and at weeks 6 and 12. In addition, the overall signs of rosacea were rated during the 12 week study using the following global assessment scale.

Rosacea Global Score:

0=Clear: absence of inflammatory sessions, erythema, and telangiectasias

1=Almost clear: absence of inflammatory lesions, or presence of a few small involuted lesions, trace of erythema, presence or absence of telangiectasias.

2=Mild: few small inflammatory lesions, mild erythema and presence or absence of telangiectasias.

3=Moderate: Moderate number of inflammatory lesions, moderate to severe erythema, presence of telangiectasias.

4=Severe: large number of inflammatory lesions, moderate to severe erythema, presence of telangiectasias.

The results of the evaluation are shown below for each of the 8 patients enrolled in the study. As shown, application of the cream of Example 7 reduced the total number of lesions for 5 of the 8 patients (63%) treated. The average eduction of lesions for the 5 patients showing an effect was 70%. The overall reduction of lesions for all 8 patients treated was 26%.

| Subject Number | Lesion Count | | | |
| --- | --- | --- | --- | --- |
| | Baseline | Week 6 | Week 12 | Reduction at Week 12 |
| 1 | 7 | 10 | 12 | 5 |
| 2 | 4 | 4 | 1 | −3 |
| 3 | 7 | 12 | 12 | 5 |
| 4 | 8 | 8 | 4 | −4 |
| 5 | 5 | 1 | 0 | −5 |
| 6 | 4 | 1 | 4 | 0 |
| 7 | 4 | 1 | 0 | −4 |
| 8 | 4 | 5 | 3 | −1 |

In a similar manner, 4 of the 8 patients showed a 50% decrease in the Rosacea Global Score, going from the "mild" to the "almost clear" category within the 12 week study period, thereby, indicating a response to the peptide copper treatment during that period.

Thus, the above examples demonstrate the effectiveness of the method the present invention in alleviating the signs and symptoms of rosacea.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, it will be appreciated that, although specific embodiments of the present invention have been described herein for purposes of illustration, various modifications may be made without deviating from the spirit and scope of the invention. Accordingly, the present invention is not limited except as by the appended claims.

The invention claimed is:

1. A composition comprising at least one peptide copper complex and an active drug substance selected from the group consisting of a corticosteroid, metronidazole, sulfacetamide, sulfur, azelaic acid and a combination thereof.

\* \* \* \* \*